US006155970A

United States Patent [19]

Dykes et al.

[11] Patent Number: 6,155,970

[45] Date of Patent: Dec. 5, 2000

[54] ROTATING INFANT MATTRESS

[75] Inventors: Christopher A. Dykes, Odenton; John B. Poling, Sparks; Thomas C. Jones, Columbia, all of Md.

[73] Assignee: Datex-Ohmeda, Inc., Tewksbury, Mass.

[21] Appl. No.: 09/119,469

[22] Filed: Jul. 20, 1998

[51] Int. Cl.$^{7}$ ........................................ A61B 5/00

[52] U.S. Cl. .............................. 600/22; 600/21; 5/610; 5/81.1 RP

[58] Field of Search .................. 600/21–22; 5/600–624, 5/81.1 RP, 93.1, 97

[56] References Cited

U.S. PATENT DOCUMENTS

| | | | |
|---|---|---|---|
| 3,326,203 | 6/1967 | Goertzel | 600/22 |
| 5,330,415 | 7/1994 | Storti et al. | 600/21 |
| 5,624,375 | 4/1997 | Dykes et al. | 600/22 |
| 5,898,817 | 4/1999 | Salmon et al. | 600/22 |

FOREIGN PATENT DOCUMENTS

| | | |
|---|---|---|
| 1239060 | 4/1967 | Germany . |

OTHER PUBLICATIONS

Brochure—Phoenix Medical Systems “Neonatal Open Care System” Phoenix 100 NRC.

*Primary Examiner*—Max Hindenburg
*Assistant Examiner*—Michael Astorino
*Attorney, Agent, or Firm*—Roger M. Rathbun

[57] ABSTRACT

An infant care apparatus such as an incubator or infant warmer having a mattress for supporting the infant on an infant platform that can, at times, by fully rotated 360 degrees to obtain full access to the infant. In the incubator, a translation platform can be slid into and out of the infant compartment and the mattress tray is pivoted to that translation platform so as to rotate at a pivot point that connects the mattress tray to the translation platform. Accordingly, when all of the doors of the infant incubator are in the closed position, the mattress tray is constrained from rotational movement but that mattress tray can be rotated a full 360 degrees whenever both doors are open or when the translation platform has been moved to a position at least partially exterior of the infant compartment. In all, the apparatus provides easy and convenient access to the infant for carrying out procedures on the infant while it is still supported by the infant care apparatus.

15 Claims, 5 Drawing Sheets

ROTATING INFANT MATTRESS

BACKGROUND

This invention relates to apparatus for containing infants, and more particularly, to an infant incubator or infant warmer having a means of achieving considerable access to the infant contained within the apparatus.

Infant incubators are basically controlled environments within which the infant is contained and wherein the temperature and humidity are controlled to provide that environment to the infant. As such, therefore, there is an infant compartment that contains the infant and where the environment is controlled to provide the correct conditions for that infant.

Infant warmers, on the other hand, are used to provide heat to the infant but the infant is not generally within a protective, enclosed environment but may be exposed to the surrounding ambient atmosphere. The infant warmer is used where the personnel need considerable access to carry out some procedure on the infant.

With the use of either infant care apparatus, however, there obviously are times that the environment of an incubator must be invaded for the attending personnel to provide some function to the infant, be it changing the infant or providing other therapy or aid the infant. At such times, the personnel must have good access to the infant and preferably be able to position the infant in a variety of positions so that the needed procedures can be carried out in an expeditious manner and the infant returned to the controlled environment. Alternatively, the infant may be fully removed from the incubator and the certain procedure carried out on a table nearby, however, that is inconvenient and it is preferable to be able to act on the infant without moving it away to a separate location. In addition, there is not only the inconvenience of moving the infant to another location but any movement of an infant that is in need of an incubator or warmer is potentially very disruptive to the infant and it is advantageous to move or disrupt the infant and the surrounding therapy device connections as little as possible.

Accordingly, there are infant incubators where the infant may be partially withdrawn from the incubator by some mechanism associated with the incubator, such as a sliding infant support that allows the infant to be moved laterally out of the incubator for the procedure, however, such systems do not allow personnel the ability to move the infant to various positions to gain access to the particular portion of the infant that requires attention. Another means of gaining access to an infant is shown and described in German DE1,239,060 where a mattress is pivoted about a point near one end of the mattress so that the infant can be swung out of the infant care apparatus for accessibility. In addition, an open care system is known of Phoenix Medical Systems Ltd. In Madras, India that has a limited rotating function to a circular bed.

It would therefore be advantageous to have an infant incubator that includes an infant support that can be moved to a large number of angular and lateral positions so that the attending personnel can have the maximum amount of access to the infant easily and reliably.

It would also be an advantage to have an infant warmer with a mattress that can be fully rotated 360 degrees about a central pivot so that the attending personnel can have maximum access with minimal disruption of the surrounding therapy device connections. It would be further advantageous for a combination of incubator and infant warmer to provide the access to the infant that a rotating and translating mattress would afford.

SUMMARY OF THE INVENTION

The present invention provides an incubator or infant warmer having a mattress upon which the infant is positioned and which can be rotated to gain almost complete access to the infant to carry out the necessary procedures upon the infant. In one embodiment of the present invention, the mechanism includes a translation platform that is positioned within the infant compartment during the normal operation of the incubator and which may be moved to a partially external position where the infant is moved laterally towards the outside the infant incubator and which is still supported by the incubator apparatus itself.

When the translation platform has thus been moved to its outer position, the infant may be rotated about a central pivot point such that the attending personnel can fully rotate the infant 360 degrees to whatever position is desired to gain access to the part of the infant where the procedure is needed.

By means of the present invention, therefore, the infant can be moved laterally to a position partially external of he incubator compartment, rotated easily, and, when the particular procedure has been completed, the infant may be readily moved back to within the controlled, protective environment of the incubator.

In an alternate embodiment, the rotating infant mattress is used in an infant warmer and the mattress rotatable 360 degrees about a central pivot point of the mattress so that complete access is afforded to perform procedures on the infant. That alternate embodiment can, of course, also provide the translation movement along a linear path and then be rotatable when the infant has been moved away from the central focus of the heater used in the infant warmer.

Other features of the rotating infant mattress will be come apparent in light of the following detailed description of a preferred embodiment thereof and as illustrated in the accompanying drawings.

DETAILED DESCRIPTION OF THE INVENTION

Figure 1:
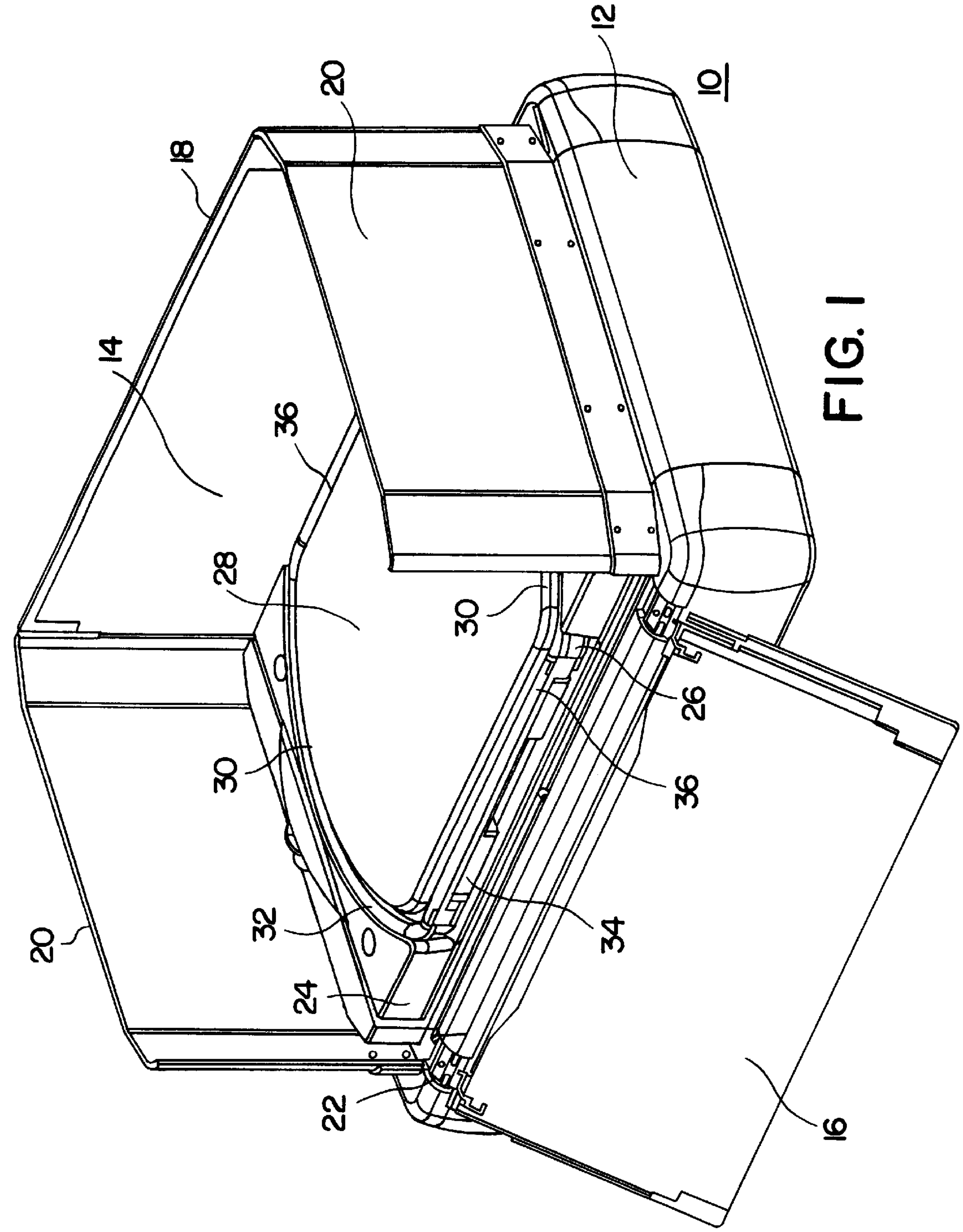
FIG. 1 is an isometric view of an incubator constructed in accordance with the present invention and having an incubator door in the open position.

Referring now to FIG. 1, there is shown an isometric view of an incubator 10 constructed in accordance with the present invention. The incubator 10 comprises a base section 12 that normally contains the heating and air ducting mechanism to provide the heated and humidified air into the infant compartment 14 that contains the infant. As shown, the incubator 10 includes a front door 16, a rear door 18 and a pair of side sections 20 that together form the infant compartment 14. As is conventional, the front door 16, rear door 18 and the side sections 20 are preferably of a transparent plastic material to allow good visibility of the infant contained therein.

In FIG. 1, the upper part of the infant compartment 14 is shown as open with the cover removed, however, in normal incubators, a cover is provided or other enclosure to insure that the infant compartment 14 is enclosed so as to maintain the infant in the enclosed, controlled environment. A typical incubator that may employ the rotating mattress features of the present invention is shown and described in U.S. Pat. No. 4,936,824 of Koch et al.

As can be seen and again which is conventional, the front door 16 is affixed to the base section 12 by means of a hinge 22 and which allows the front door 16 to be opened by the user. Although not shown, the rear door 18 can be secured in the same manner. Within the infant compartment, there is located a translation platform 24 and which may rest upon a flat, planar surface separating the base section 12 from the infant compartment 14 in a manner to be later described.

Rotatably mounted to the translation platform 24 is a mattress tray 26 for supporting the infant within the infant compartment 14. A mattress 28 fits within the mattress tray 26 for comfort of the infant. As can be noted in FIG. 1, the mattress tray 26 is generally rectangular and has its shorter, opposed ends 30 radiused to fit within corresponding radiused sides 32 of the translation platform 24. An X-ray tray 34 also fits underneath the mattress tray 26 as will be explained.

Figure 2:
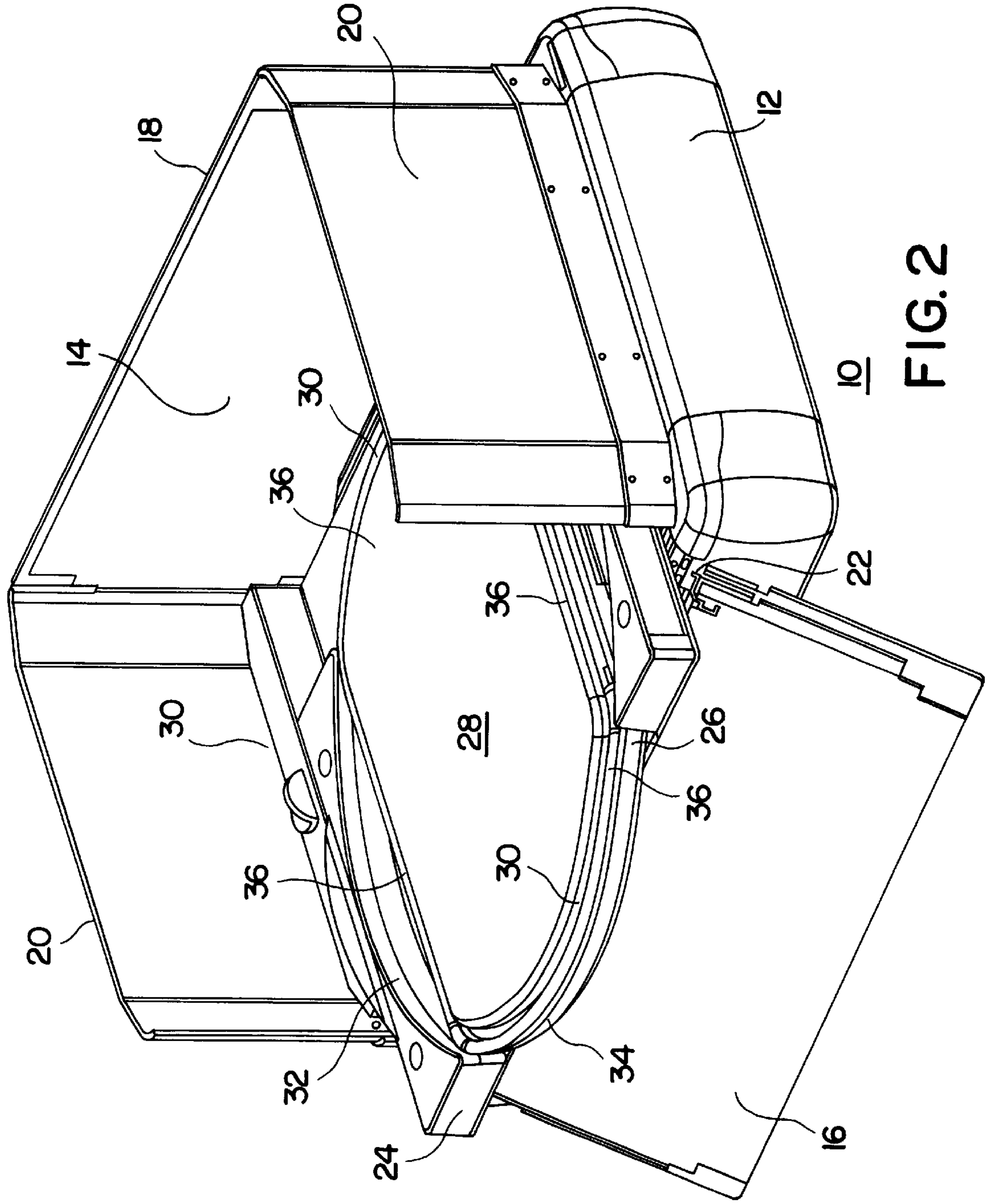
FIG. 2 is an isometric view of the incubator of FIG. 1 wherein the incubator mattress has been translated and rotated to its partially exterior position.

Turning now to FIG. 2, there is shown an isometric view of the incubator 10 of the present invention and wherein the translation platform 24 has been moved along its minor axis to a position where it is at least partially removed from the infant compartment 14. Thus, in the position as shown, the translation platform 24 is in a partially exterior position where the straight sides 36 of the mattress tray 26 are no longer constrained by the inner surfaces of the front door 16 and the rear door 18 such that the mattress tray 26 can be rotated about a central pivot point. In FIG. 2, the mattress tray 26 has been rotated about ninety degrees and thus the head or feet of the infant can fully extend out of the incubator 10 for complete access to that portion of the infant.

As will become apparent, once the translation platform 24 has been moved to the exterior position shown in FIG. 2, the mattress tray 26 can be rotated at will so that the attending personnel can position the infant at any position around 360 degrees of rotation.

Figure 3:
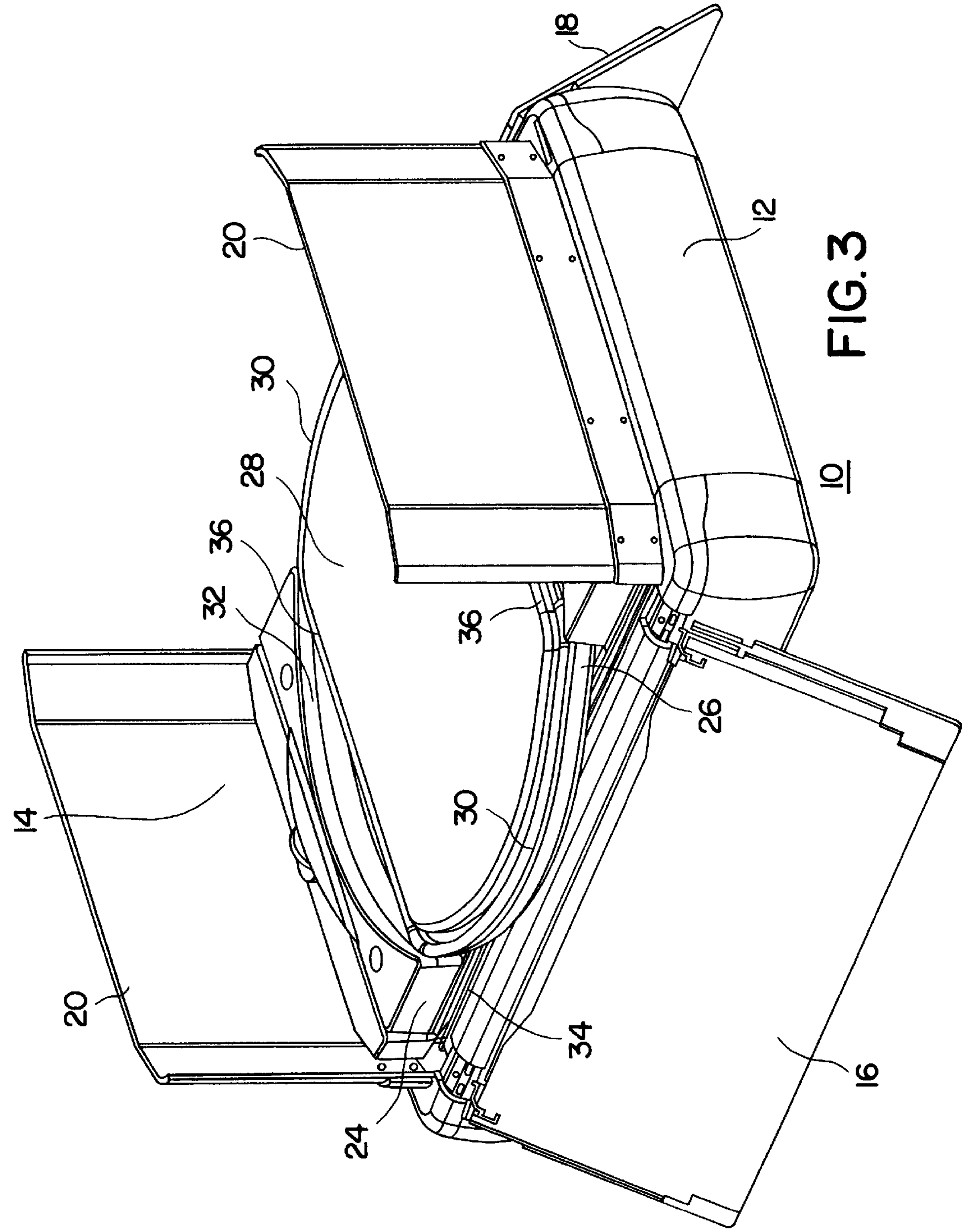
FIG. 3 is a isometric view of the incubator of FIGS. 1 and 2 with opposite doors in the open positions with the mattress rotated 90 degrees.

Turning now to FIG. 3, there shown an isometric view of an incubator 10 constructed in accordance with the present invention and wherein the front door 16 and the rear door 18 are both in the open position. As can be seen, the straight sides 36 of the mattress tray 26 are thus no longer constrained by the physical obstruction offered by the presence of the front door 16 and the rear door 18 that are normally located adjacent the straight sides 36 of the mattress tray 26 and prevent the mattress tray 26 it from being rotated while within the infant compartment 14. Accordingly, the mattress tray 26 can be rotated by translating it to its partially exterior extended position.

In addition, the mattress tray 26 and thus, the infant, can be rotated 360 degrees while still within the confines of the infant compartment 14 when both of the front and rear doors 16 and 18 are in the open position so that they no longer obstruct the straight sides 36 of the mattress tray 26 from rotating. As can be seen, if either one of the doors adjacent the two straight edges of the mattress tray 26 are in the closed position, the mattress tray 26 cannot be rotated unless it is further translated to the partially exterior position.

Figure 4:
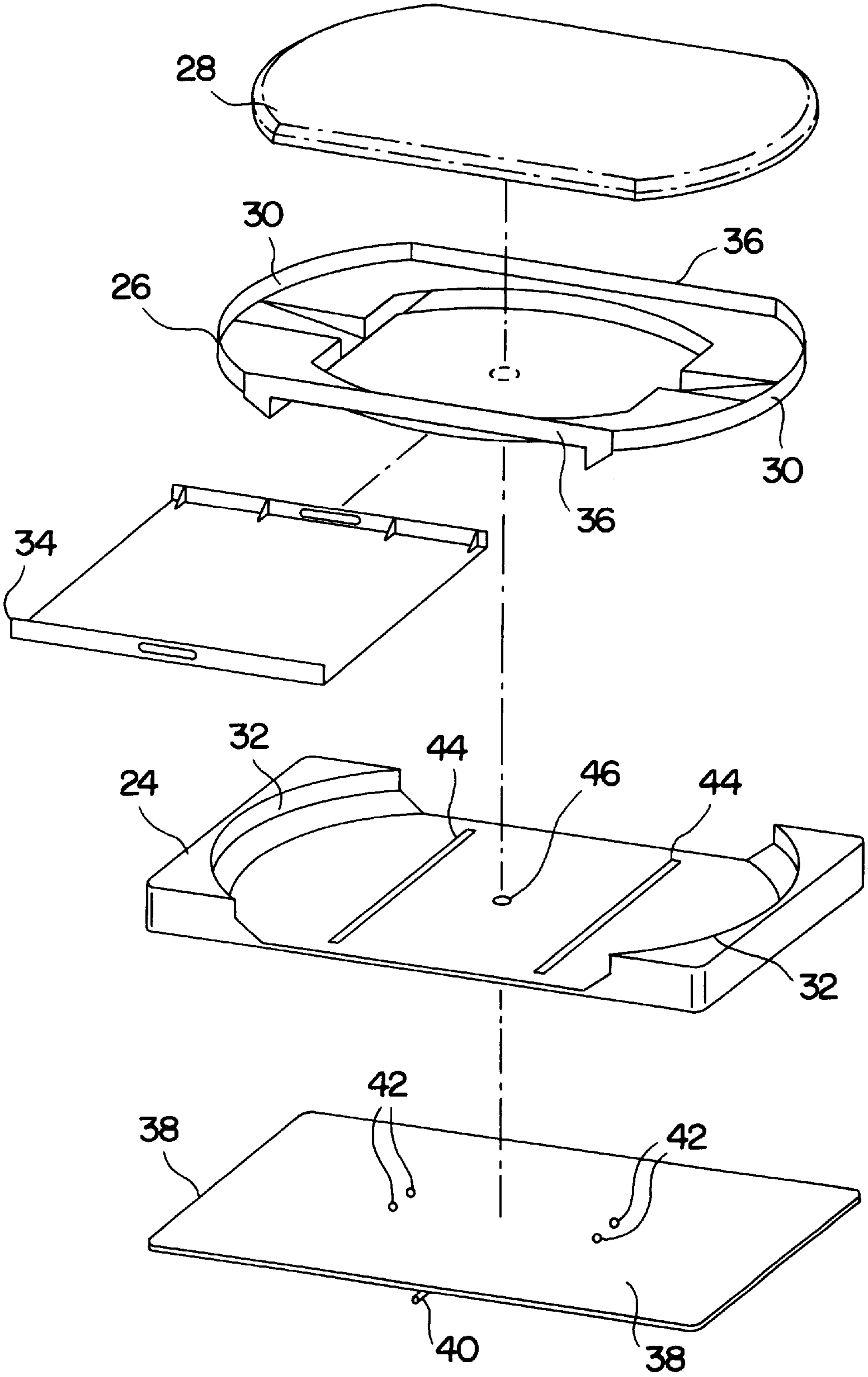
FIG. 4 is an exploded view of the rotating mattress mechanism of the present invention.

Turning now to FIG. 4, there is shown an exploded view of the infant incubator 10 of the present invention and showing the components for the preferred embodiment for allowing rotation of the infant. A flat planar tilt platform 38 is positioned beneath the infant mattress 28 and separates the infant compartment 14 from the base section 12 containing the ventilation equipment. The tilt platform 38 is normally tiltable by various means and, as an example, there is shown a pair of pins 40 projecting outwardly from the planar base 38 along the major axis and the pins 40 can form pivot points for the planar base 38 and interfit with some corresponding function, such as a notch, formed in the base section 12 such that the tilt platform 38 is tiltable about the pins 40.

As can be seen, the translation platform 24 fits atop of the tilt platform 38 and can be moved along that surface of the tilt platform 38. In particular, the translation platform 24 is movable along its minor axis, that is, it is movable in a direction parallel to its shortest ends and that movement is constrained by the interfitting with a parallel set of stubs 42 that fit within slots 44 formed in the translation platform 24. Thus, the movement of the translation platform 24 is guided by the stubs 42 so that the translation platform 24 cannot become misaligned during movement and its total movement.

Accordingly returning briefly to FIGS.1–3, it can be seen that the translation platform 24 is readily movable along its minor axis to move the infant mattress 28 between a position where the mattress tray 26 is fully within the infant compartment 14, and the front and rear doors 16 and 18 can be in the closed position, and a position where the mattress tray 26 is at least partially exterior of the infant compartment out the front door 16. Returning to FIG. 4, the mattress tray 26 is rotatably affixed to the translation platform 24 such that it can rotate 360 degrees and such means may be a pivot 46 of conventional design that is, of course, located at the center of the translation platform 24 and the mattress tray 26. The mattress 28 fits within the mattress tray 26 to provide a comfortable support for the infant.

Therefore, as seen in FIG.4, the translation platform 24 is movable or translated in a direction along its minor axis to move the translation platform 24, along with the mattress tray 26 and mattress 28 into and out of the infant compartment 14 to a position partially exterior of the infant compartment 14. At the same time, the mattress tray 26 is fully rotatable with respect to the translation platform 24, having its radiused ends 30 interfitted closely with the similarly radiused sides 32 of the translation platform 24. The straight sides 36 of the mattress tray 34 are formed such that the mattress tray 34 can fit within the generally rectangular infant compartment , however, as is now apparent, when both doors are closed, FIG. 1, the straight sides 36 of the mattress tray 26 are generally adjacent each of the front and the rear doors 16 and 18 such that rotation is not possible with the doors closed. The front and rear doors 16 and 18, when closed, simply obstruct the movement of the straight sides 36 to prevent rotation of the mattress tray 26.

On the other hand, when both doors are in the open position, FIG. 3, the mattress tray 26 is fully rotatable even when the translation platform 24 has not been moved to its partially or fully open exterior position but is still within the infant compartment 14. That is due to the absence of the normally obstructing surfaces of the doors when they are juxtaposed alongside the straight edges of the mattress tray 26.

As a final component, in FIG. 4, the X-ray tray 34 is slidably mounted intermediate the mattress tray 26 and the translation platform 24 and can be slid in and out of that position to accommodate the introduction and removal of X-ray film for taking X-rays of the infant without moving the infant on the mattress 28.

Figure 5:
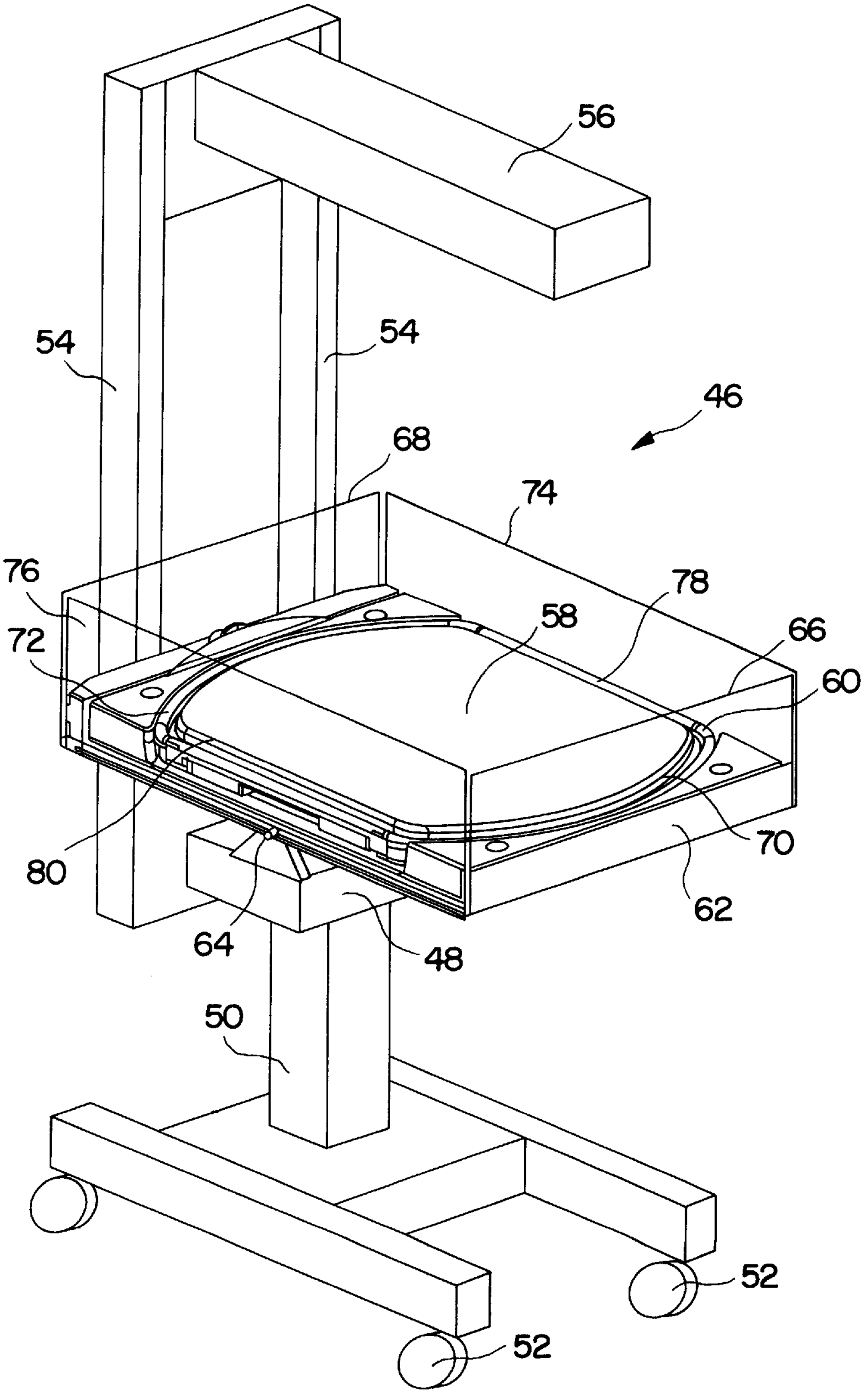
FIG. 5 is an isometric view of an infant warmer embodiment utilizing the rotating mattress constructed in accordance with the present invention.

Turning finally to FIG. 5, there is shown an isometric view of an infant warmer 46 constructed in accordance with the present invention. In FIG. 5 the infant warmer may be similar to that shown and described in U.S. Pat. No. 4,628,553 and comprises a base 48 that may include a pedestal 50 having wheels 52 so that the infant warmer 46 is readily movable. Vertical struts 54 support the heater unit 56 and which may be a quartz heater that provides the heat directly downwardly towards an infant resting upon a mattress 58 that, again, is supported by a mattress tray 60. The mattress tray 60 is, in turn, is supported by an infant bed 62 that is pivotally mounted to the base 48 at a pivot point 64 so that the infant bed 62 can be tilted to, and retained at, various tilt angles desired by the user.

As can also be seen, the infant warmer 46 preferably has a plurality of guards, normally constructed of a clear plastic, that protect the infant from inadvertently falling out of the apparatus and those are illustrated as front and back guards 66 and 68 that are along the shorter, radiused sides 70 and 72 of the mattress tray 60, and side guards 74 and 76 that generally abut and are juxtaposed along the straight sides 78, 80 of the mattress tray 60. In the infant warmer 46, the front and back guards 66 and 68 as well as the side guards 74 and 76 are pivoted at their lower edges to the infant bed 62 such that they may be dropped to a lowered position where the user can have complete access to the infant lying upon the mattress 58 without having to reach over the various guards. The operation of the sides of a typical infant warmer can be seen in the aforementioned U.S. Pat. No. 4,628,553 and the mechanism is conventional and readily available.

As can now be seen, the infant warmer 46 can be operated in the same manner as the incubator of FIGS. 1–4 to the extent of gaining access to an infant by manipulation of the mattress tray 60. The same mechanism that is shown and described with respect to FIGS. 1–4 underlies the mattress tray 60 of FIG. 5 and thus the mattress tray 60 can be translated to a position partially removed from the position shown in FIG. 5 centrally located beneath the heater unit 56. At the removed or translated position, the mattress tray 60 may be fully rotated 360 degrees about the central pivot point. Similarly, the user can retain the mattress tray 60 in its position of FIG. 5 but drop the side guards 74 and 74 and still be able to rotate the mattress tray 60 a full 360 degrees about the central pivot point to gain whatever access is needed to the infant. Again, as noted, if either of the side guards 74 or 76 are not dropped, that is, either is in the upper position shown in FIG. 5, it is not possible to rotate the mattress tray 60 without also translating the mattress tray 60 partially out from its FIG. 5 position since the side guards 74,76, each are juxtaposed along the straight sides 78, 80 of the mattress tray 60 and obstruct the rotation of the mattress tray 60.

While the present invention has been set forth in terms of a specific embodiment, it will be understood that the rotating mattress mechanism herein disclosed may be modified or altered by those skilled in the art to other configurations. Accordingly, the invention is to be broadly construed and limited only by the scope and spirit of the claims appended hereto.

We claim:

1. An infant compartment for containing an infant, said infant compartment comprising a base and a mattress tray supported on said base, a hood covering said mattress tray and supported on said base to enclose therein said infant compartment, said hood having an opening and a front door openable and closable with respect to said opening, mounting means adapted to mount said mattress tray to said base to rotate in a plane about a point and movable along a line to enable said mattress tray to move through said opening between an internal position wherein it is fully within said infant compartment and an external position wherein said mattress tray is at least partially positioned external of said infant compartment, said mounting means allowing the rotation of said mattress tray when said mattress tray is in said external position.

2. An infant compartment for containing an infant as defined in claim 1 wherein said hood has a pair of doors oppositely positioned with respect to each other, each having open and closed positions.

3. An infant compartment for containing an infant as defined in claim 2 wherein said mattress tray has oppositely disposed straight edges generally along and in close proximity to said pair of doors to prevent said mattress tray from rotational movement when said doors are in the closed position but to allow rotation when said doors are both in the open positions.

4. An infant compartment for containing an infant as defined in claim 2 wherein said mattress tray is generally rectangular having four sides and wherein two sides have straight sides along said doors and two sides are generally curved.

5. An infant compartment for containing an infant as defined in claim 2 wherein said curved sides of said mattress tray are both circular having the same radii and having said pivot point as the center of said radii.

6. An infant incubator for enclosing an infant in a controlled environment, said infant incubator having a base section and a hood covering said base section and enclosing therebetween an infant compartment for containing an infant, said incubator having a planar platform separating said infant compartment and said base section, a translation tray slidably mounted atop said planar platform and adapted to be movable between a position within said infant compartment to a position at least partially exterior of said infant compartment, a mattress tray having a mattress for underlying and supporting an infant, said mattress tray rotatably affixed to said translation tray about a pivot point, said mattress tray being rotatable in a plane about said pivot point to rotate the infant supported thereon to multiple positions about said pivot point for access by an attendant.

7. An infant incubator as defined in claim 6 wherein said mattress tray is generally rectangular having radiused ends and straight ends and said mattress tray is movable along its minor axis.

8. An infant incubator as defined in claim 7 wherein said infant incubator hood includes a front door and a rear door and said straight ends of said mattress tray are in alignment with said front and rear doors when said mattress tray is in said position within said infant compartment.

9. An infant incubator as defined in claim 6 wherein said mattress tray moves along its minor axis to its at least partially exterior position through said front door wherein said mattress tray is rotatable about said pivot point to provide access to an infant positioned on said mattress tray.

10. An infant incubator as defined in claim 8, wherein said front door and said back door have open positions and closed positions and wherein said front and said rear doors block the rotation of said mattress tray about said pivot point when said front door and said rear door are in the closed position.

11. An infant care apparatus for supporting an infant, said infant care apparatus comprising a base and a mattress tray supported on said base, means to provide heat to the infant supported on said mattress tray, mounting means adapted to mount said mattress tray to said base to be rotatably movable about a central pivot point to enable said mattress tray to rotate 360 degrees about said central pivot point.

12. An infant care apparatus as defined in claim 11 wherein said infant care apparatus is an infant warmer and said mattress tray is generally rectangular with two opposite sides radiused and two opposite sides are straight.

13. An infant care apparatus as defined in claim 12 wherein said base includes a plurality of guards that surround the periphery of said mattress tray, said guards having a n upper position in which said guards depend upwardly to contain an infant on said mattress tray and a lower position where said guards are removed from protecting the infant.

14. An infant care apparatus as defined in claim 13 wherein said straight sides of said mattress tray generally are juxtaposed along at least one of said guards and said at least one said guards obstructs said mattress tray from rotating when said at least one of said guards is in said upper position.

15. An infant care apparatus as defined in claim 11 wherein said mounting means includes means to translate said mattress tray along a straight linear path.

* * * * *